US010967052B1

(12) United States Patent
Williams

(10) Patent No.: US 10,967,052 B1
(45) Date of Patent: Apr. 6, 2021

(54) TREATMENT OF DYSLEXIA USING BOTULINUM TOXIN

(71) Applicant: PENLAND FOUNDATION, Beaumont, TX (US)

(72) Inventor: Roland M. Williams, Beaumont, TX (US)

(73) Assignee: PENLAND FOUNDATION, Beaumont, TX (US)

( * ) Notice: Subject to any disclaimer, the term of this patent is extended or adjusted under 35 U.S.C. 154(b) by 0 days.

(21) Appl. No.: 16/875,912

(22) Filed: May 15, 2020

Related U.S. Application Data

(63) Continuation-in-part of application No. 16/657,933, filed on Oct. 18, 2019, and a continuation-in-part of application No. 16/657,950, filed on Oct. 18, 2019.

(51) Int. Cl.
*A61K 38/48* (2006.01)
*A61K 9/00* (2006.01)
*A61P 25/28* (2006.01)

(52) U.S. Cl.
CPC ........ *A61K 38/4893* (2013.01); *A61K 9/0085* (2013.01); *A61P 25/28* (2018.01); *A61K 9/0021* (2013.01); *C12Y 304/24069* (2013.01)

(58) Field of Classification Search
None
See application file for complete search history.

(56) References Cited

U.S. PATENT DOCUMENTS

| | | | |
|---|---|---|---|
| 5,766,605 A | 6/1998 | Sanders et al. | |
| 6,063,768 A | 5/2000 | First | |
| 6,139,845 A | 10/2000 | Donovan | |
| 6,632,440 B1 | 10/2003 | Quinn et al. | |
| 6,977,080 B1 | 12/2005 | Donovan | |
| 7,655,244 B2 | 2/2010 | Blumenfeld | |
| 8,734,810 B2 | 5/2014 | Blumenfeld | |
| 9,254,314 B2 | 2/2016 | Finzi et al. | |
| 9,707,207 B2 | 7/2017 | Finegold | |
| 10,011,823 B2 | 7/2018 | Barbieri et al. | |
| 10,258,673 B2 | 4/2019 | Pokushalov et al. | |
| 10,722,552 B1 | 7/2020 | Williams | |
| 2004/0062776 A1 | 4/2004 | Voet | |
| 2004/0220544 A1 | 11/2004 | Heruth et al. | |
| 2005/0147626 A1 | 7/2005 | Blumenfeld | |
| 2005/0191320 A1 | 9/2005 | Turkel et al. | |
| 2007/0259002 A1 | 11/2007 | Batchelor | |
| 2009/0142430 A1 | 6/2009 | Sanders et al. | |
| 2009/0232850 A1 | 9/2009 | Manack et al. | |
| 2010/0303788 A1 | 12/2010 | Francis et al. | |
| 2011/0200639 A1 | 8/2011 | Blumenfeld | |
| 2012/0093827 A1 | 4/2012 | Van Schaack et al. | |
| 2012/0195878 A1 | 8/2012 | Haag-Molkenteller et al. | |
| 2012/0244188 A1 | 8/2012 | Blumenfeld et al. | |
| 2012/0251519 A1 | 10/2012 | Blumenfeld et al. | |
| 2013/0251830 A1 | 9/2013 | Manack et al. | |
| 2015/0086533 A1 | 3/2015 | Borodic | |
| 2017/0173123 A1 | 6/2017 | Blumenfeld | |
| 2017/0333537 A9 | 11/2017 | Borodic | |
| 2018/0071361 A1 | 3/2018 | Abiad et al. | |
| 2019/0038646 A1 | 2/2019 | Bright et al. | |
| 2019/0300583 A1 | 10/2019 | Jarpe | |

FOREIGN PATENT DOCUMENTS

| | | |
|---|---|---|
| EP | 2072039 A1 | 6/2009 |
| JP | 2012107051 A | 6/2012 |
| KR | 20100032982 A | 3/2010 |
| KR | 20150126979 A | 11/2015 |
| WO | WO 95/28171 | 10/1995 |
| WO | WO 00/10598 | 3/2000 |
| WO | WO 01/104058 A | 2/2001 |
| WO | WO2010013495 A1 | 2/2010 |
| WO | WO2011084507 A | 7/2011 |
| WO | WO2014184746 A | 11/2014 |

OTHER PUBLICATIONS

Saunte, Acta Ophthalmologica (1755375X). Aug. 2015, vol. 93 Issue 5, p. e391-e392 (Year: 2015).*
The WebMD website, https://www.webmd.com/children/dyslexia-treatments; accessed Jun. 22, 2020 (Year: 2020).*
Hulme et al., Curr Opin Pediatr 2016, 28: 731-735 (Year: 2016).*
Pugh et al., J. Neurosci., 2014; 34(11): 4082-4089 (Year: 2014).*
The article downloaded Nov. 30, 2020 from https://www.webmd.com/add-adhd/adhd-dyslexia-tell-apart?print=true; 3 pages total (Year: 2020).*
Machine translation of the WO2010/013495 document; 25 pages total (Year: 2021).*
Pugh KR et al, Abstract—"Glutamate and choline levels predict individual differences in reading ability in emergent readers", J.Neurosci. Mar. 12, 2014;34(11):4082-9. doi: 10.1523/JNeurosci. 3907-13.2014 https://www.ncbi.nlm.nih.gov/pubmed/24623786 (Dec. 13, 2019).
Ryan J. Diel, MD et al, "Photophobia and sensations of dryness in migraine patients occur independent of baseline tear volume and improve following botulinum toxin A injections", HHS Public Access, Br J Ophthalmol. Author manuscript; available in PMC Aug. 1, 2019, pp. 1-15.
Donald C. Rojas, "The role of glutamate and its receptors in autism and the use of glutamate receptor antagonists in treatment", J Neural Transm. Aug. 2014 ; 121(8): 891-905, pp. 1-24
Juan M. Espinosa-Sanchez et al, "New insights into pathophysiology of vestibular migraine", Frontiers in Neurology, Feb. 2015 l vol. 6 l Article 12, pp. 1-6.

(Continued)

*Primary Examiner* — Christina M Borgeest
(74) *Attorney, Agent, or Firm* — Winston & Strawn LLP

(57) ABSTRACT

A method for treating dyslexia or reading developmental disorder (RDD) in a patient in need thereof comprises administering botulinum toxin to the patient. The botulinum toxin may be administered by subcutaneous or intradermal injection. The subcutaneous or intradermal injection may be administered to and/or around the vicinity of a trigeminal nerve, a cervical nerve, a thoracic nerve, a lumbar nerve, and/or a sacral nerve of the patient. In infants or toddlers— from about birth to 5 years old, botulinum toxin is used to prevent or minimize damage to the developing brain that would result in dyslexia; in older children and adult patients with dyslexia, botulinum toxin will be used to reduce or eliminate their symptoms.

20 Claims, No Drawings

(56) References Cited

OTHER PUBLICATIONS

Colleen Doherty, MD, "The Link Between Migraines and Tinnitus, Buzzing or ringing in your ears could be related to your episodes", VeryWell Health, Aug. 6, 2019, pp. 1-13 https://www.verywellhealth.com/link-between-migraines-and-tinnitus-4077631.

K,J. Powell et aL, "The Role of CGRP in the Development of Morphine Tolerance and Physical Dependence", 4th International Meeting on Calcitonin Gene-Related Peptide (CGRP), the ScientificWorld (2001) 1 (S1), 21. 2 pages.

Vacca et al., "Botulinum Toxin A Increases Analgesic Effects of Morphine, Counters Development of Morphine Tolerance and Modulates Glia Activation and μ Opioid Receptor Expression in Neuropathic Mice", Brain, Behavior, and Immunity 32 (2013), pp. 40-50 (Year: 2013).

Mayo clinic article, "Autism Spectrum Disorder", Symptoms and Causes, 5 pages (Year: 2019) downloaded on Dec. 23, 2019 from: https://www.mayoclinic.org/diseases-conditions/autism-spectrum-disorder/ symptoms-causes/ syc-20352928?p=1.

The Machine Translation of WO2010013495, English Abstract,"Pharmaceutical Composition Containing Highly Purified Botulinum Neurotoxin Therapeutic Agent as Active Ingredient, and Use Thereof", Akaike et al.; Feb. 4, 2010 (Year: 2010).

Nair et al., "Impaired Thalamocortical Connectivity in Autism Spectrum Disorder: A Study of Functional and Anatomical Connectivity", Brain, Journal of Neurology, 2013; 136: 1942-1955 (Year: 2013).

Panju et al., "Atypical Sympathetic Arousal in Children With Autism Spectrum Disorder and Its Association With Anxiety Symptomatology", Molecular Autism (2015) 6:64, pp. 1-10 (Year: 2015).

Saunte et al., "Improverment in Reading Symptoms Following Botulinwn Toxin A Injection for Convergence Insufficiency Type Intermittent Exotropia", Acta Ophthalmologica (1755375X). Aug. 2015, vol. 93 Issue 5, pp. 1-3 (Year: 2015).

Mazzone et al., "Vaginal Afferent Innervation of the Airways in Health and Disease", Physiol Rev 96: 975-1024, 2016, pp. 975-1024, (Year: 2016).

Schematic of innervation of organs, available from https://ars.els-cdn.com/content/image/3-s2.0-B9780323378048000055-f005-001-9780323378048.jpg, downloaded Jun. 22, 2020 and reproduced within the Office action (Year: 2020).

The Harvard Medical School , "Cardiac Arrhythmias", Harvard Health Publishing, Published Feb. 2019, website; downloaded Jul. 18, 2020 from: https://www.health.harvard.edu/a_to_z/ cardiac-arrhythmias-a-to-z; 5 pages total (Year: 2020).

Machine English Translation of the foreign patent document, KR20100032982, 7 pages total (Year: 2010).

Mitchell and Borasio et al., "Amyotrophic Lateral Sclerosis", Seminar, Lancet 2007; vol. 369: 12 pp. 2031-2041 (Year: 2007).

Oomens and Forouzanfare t al., "Pharmaceutical Management of Trigeminal Neuralgia in the Elderly", Review Article Drugs Aging (2015) 32: pp. 717-726 (Year: 2015).

S. Kumar, "The Emerging Role of Botulinum Toxin in the Treatment of OroFacial Disorders: Literature Update", Asian Journal Pharm Clin Res, vol. 10, Issue 9, 2017, pp. 21-29 (Year: 2017).

Lewitt and Trosch, et al., "Idiosyncratic Adverse Reactions to Intramuscular Botulinum Toxin Type A Injection", Movement Disorders, 1997; 12: pp. 1064-1067 (Year: 1997).

Squires et al., "The Use of Botulinum Toxin Injections to Manage Drooling in Amyotrophic Lateral Sclerosis/Motor Neurone Disease: A Systematic Review", Dysphagia (2014) 29: pp. 500-508 (Year: 2014).

The website downloaded on Jul. 2, 2020 from Juvenile Amyotrophic Lateral Sclerosis,Genetic and Rare Diseases Information Center (GARD)—an NCATS Program, https://rarediseases.info.nih.gov/diseases/11901/juvenile-amyotrophic-lateral-sclerosis; Jul. 2, 2020, 8 pages total (Year: 2020).

Mortazavi et al., "Xerostomia Due to Systemic Disease: A Review of 20 Conditions and Mechanisms", Ann Med Health Sci Res. Jul-Aug. 2014; 4(4): 503-510, doi: 10.4103/2141-9248.139284: 10.4103/2141-9248.139284 , 15 pages Year: 2014).

The website downloaded Jul. 21, 2020 from Children's Hospital of Pittsburgh , "Cirrhosis in Children: Symptoms and Treatment", UPMC, 4 paegs total . Jul. 21, 2020 (Year: 2020) (https://www.chp.edu/our-services/transplant/liver/ education/liver-disease-states/ cirrhosis.

Frank CT Smith, "Hyperhidrosis", Vascular Surgery-II, 2013; 31: pp. 251-255; doi: https://doi.org/10.1016/jmpsur.2013.03.005 (Year: 2015).

Fernandez-Rodriguez et al., "Plasma Levels of Substance P in Liver Cirrhosis: Relationship to the Activation of Vasopressor Systems and Urinary Sodium Excretion", Hepatology, Jan. 1995; 21: pp. 35-40,(Year: 1995).

Glatte et al., "Architecture of the Cutaneous Autonomic Nervous System", Frontiers in Neurology, vol. 10, Article 970, Sep. 2019, pp. 1-11, 10: doi: 10.3389/fneur.2019.00970 (Year: 2019).

Web Article: Neuroscience, what-when-how, in Depth Tutorials and Information, Gross Anatomy of the Brain, Dec. 7, 2020, 2 pages, The autonomic system schematic downloaded Nov. 23, 2020 from http://what-when-how.com/neuroscience/ the-autonomic-nervous-system-integrative-systems-part-1/; the image is reproduced in the Office action (Year: 2020).

Web Article, The image downloaded Dec. 4, 2020 from https://nursing-skills.blogspot.com/2014/01/angle-of-injection.html; image reproduced in Office action (Year: 2020.

Chien et al., "Sympathetic Fiber Sprouting in Chronically Compressed Dorsal Root Ganglia Without Peripheral Axotomy", NIH Public Access, Author Manuscript of J. Neuropathic Pain Symptom Palliation. 2005; 1 (1 ): pp. 19-23 (Year: 2005).

Scott and Fryer, "Role of Parasympathetic Nerves and Muscarinic Receptors in Allergy and Asthma", NIH Public Access, Author Manuscript of Chem Immunol Allergy. 2012; 98: pp. 48-69 (Year: 2012).

Dobrek and Thor, "Glutamate NMDA Receptors in Pathophysiology and Pharmacotherapy of Selected Nervous Dseases", Postepy Hig Med Dosw (online), 2011; 65: pp. 338-346 , 1 Year: 2011).

Erle CH Lim, "Botulinum toxin, Quo Vadis?", Elsevier Ltd., Medical Hypotheses (2007) 69, pp. 718-723 (Year: 2007) http://inti.elsevierhealth.com/journals/ mehy.

International Search Report and Written Opinion, PCT/US2020/056206, dated Feb. 1, 2021.

\* cited by examiner

US 10,967,052 B1

TREATMENT OF DYSLEXIA USING BOTULINUM TOXIN

This application is a continuation-in-part of U.S. patent application Ser. No. 16/657,933 and U.S. patent application Ser. No. 16/657,950, filed Oct. 18, 2019, respectively. The entirety of each prior application is expressly incorporated herein by reference thereto.

FIELD OF THE INVENTION

The present invention generally relates to methods for diagnosing and treating (including alleviating and/or preventing) dyslexia or reading developmental disorder (RDD) and improving the dyslexic symptoms of children and adults with botulinum toxin.

BACKGROUND OF THE INVENTION

Botulinum toxins cleave and destroy a protein called synaptosomal nerve-associated protein 25 ("SNAP25") and/or synaptobrevin (also called vesicle-associated membrane protein ["VAMP"]). Botulinum toxins A, C, and E cleave SNAP25 at different locations, but the effect is in general the same—the protein is destroyed and cannot function until the cell makes new ones. Botulinum toxins B, D, F and G cleave VAMP present at the cytoplasmic surface of the synaptic vesicle. The two important locations in the body where the proteins are found are at the terminals of the motor neurons (muscle) and in the cell membranes of astrocytes, glial cells, and satellite cells. These three cell types surround sensory neurons and form part of the blood-brain barrier. In motor nerves, to cause them to fire, vesicles of acetylcholine move from inside the motor neuron across the cell membrane at the synapse between the motor nerve and muscle fiber. Acetylcholine is released into the synapse and activates receptors in the muscle fiber, which contracts the muscle fiber. In sensory nerves, when a nerve is damaged from physical or mental injuries, the three aforementioned structural cells produce large amounts of Substance P, Calcitonin Gene Related Peptide (CGRP), and glutamate internally and the molecules are moved by vesicles to the cell membrane where the SNAP25 and/or VAMP moves the molecules through the cell membrane and releases the molecules into the cerebrospinal fluid that surrounds the neurons. There, the molecules bind to the receptor on the sensory nerves, causing the neuroexcitatory effects. The molecules can also diffuse in the cerebral spinal fluid (CSF) and influence other sensory nerves to become hyperactive, a process called central sensitization.

This mechanism of cleaving the SNAP25 and/or VAMP in muscles and sensory nerves causes the only known clinical effects of botulinum, which paralyzes muscles in the motor system for 3-4 months until the cell grows a new protein. This effect has been used for decades for overactive muscles (such as to treat overactive muscles as part of cervical dystonia, blepharospasm, tic, Parkinson's, cerebral palsy, etc.), wrinkles in the face, excessive sweating, and overactive bladder.

In the sensory nerves, the mechanism has been used for migraines and depression. The effect of blocking the SNAP25 and/or VAMP in the glial, satellite, and astrocyte cells will work for 5-9 months until these cells grow new proteins. The important part of this mechanism is that the botulinum effect does not destroy cells and does not stop the normal production of or effects of acetylcholine (muscles) or Substance P, CGRP, or glutamate in sensory nerves. These facts give huge advantages over a monoclonal antibody which would eliminate all glutamate, CGRP, and Substance P. Side effects of such elimination would be disastrous. The receptor antagonists also have problems—for example, because the receptor antagonists are not site-specific, they block glutamate, Substance P, and CGRP everywhere. Too little glutamate, Substance P, and CGRP is a problem, as well as too much. It is difficult to regulate oral or I.V. doses to obtain the correct level of reduction in areas that are too high in glutamate, Substance P, and/or CGRP without over-reduction in areas with normal levels.

Small doses of botulinum toxin injected into a specific muscle can cleave SNAP25 and/or VAMP to calm the muscle's overreaction or paralyze the muscle temporarily if desired. Or, if injected subcutaneously near unmyelinated sensory nerves, the botulinum toxin can stop the overproduction of the sensory neuroexcitatory compounds without affecting normal glutamate, Substance P, and CGRP production and function. It is, however, noted that botulinum toxin is highly lethal. Botulinum toxin is the most toxic poison known. One molecule of botulinum toxin destroys one protein molecule of SNAP25 and/or VAMP. A little bit goes a long way. Its production, storage and injection must be done with knowledge and care.

In particular, the mechanism of the sensory effect (stopping overproduction of glutamate, Substance P, and CGRP) is as follows: almost all nerves in the human body are surrounded by a protective coating called myelin, which protects the nerve and makes neural conduction faster. Botulinum toxin has difficulty penetrating the myelin. Just under the skin are sensory pain nerves called C-fibers, which are unmyelinated. Research has shown that very low dose botulinum toxin can penetrate these axons and diffuse up the axon to the cell body into the CSF and affect the SNAP25 and/or VAMP on the glial, satellite, and astrocyte cells. Subsequently, botulinum toxin destroys the SNAP25 and/or VAMP and prevents the release of the excess Substance P, CGRP, and glutamate, which is involved in a response mechanism to neural-injury without affecting normal glutamate, Substance P, and CGRP production, use, or receptors. An example of a malfunction with the normal nerve mechanism is an infection of a nerve by the shingles virus. The infection by the shingles virus damages the nerve but does not kill it, or there would be no feeling (numbness). This causes a spike in the production of glutamate, Substance P, and CGRP. This causes the well-known shingles pain and hypersensitivity. Over a 2-3 month period, the infection is controlled, the nerve heals, and the overproduction of the neuroexcitatory chemicals gets back to normal. However, sometimes for unknown reasons, the overproduction does not get back to normal but remains high, and severe chronic pain and hypersensitivity persists. Chronically overstimulated neurons can cause numerous problems depending on where the neurons are located. The neuroexcitatory chemicals can travel up the spinal cord to the brain in the CSF and affect neurons there. This process is called central sensitization. Depending on where glutamate, Substance P, and CGRP are produced and where the molecules travel to, the molecules can cause chronic pain, headaches, vertigo, sensitivity to light, sensitivity to touch, cold sensitivity, overactive bladder, depression, anxiety, flashbacks, mental fogginess, vasoconstriction of extremities, sleep disturbances, and perhaps the death and malformation of the developing neural architecture in children with ASD (autism).

SUMMARY OF THE INVENTION

The claimed invention is related to methods for treating dyslexia or reading developmental disorder (RDD) in a patient in need thereof. The method comprises administering botulinum toxin to the patient. The botulinum toxin may be administered by subcutaneous or intradermal injection. The subcutaneous or intradermal injection may be administered to and/or around the vicinity of a trigeminal nerve of the patient. The selected trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. The subcutaneous or intradermal injection may be administered to and/or around the vicinity of a cervical nerve of the patient. The selected cervical nerve comprises the c-2 nerve, c-3 nerve, c-4 nerve, c-5 nerve, c-6 nerve, c-7 nerve, c-8 nerve, or a combination thereof. The subcutaneous or intradermal injection may be administered by subcutaneous or intradermal injection to and/or around a vicinity of a thoracic nerve of the patient. The selected thoracic nerve comprises the t-2 nerve, t-3 nerve, t-5 nerve, t-6 nerve, t-7 nerve, t-8 nerve, t-9 nerve, t-10 nerve, t-11 nerve, t-12 nerve, or a combination thereof. The subcutaneous or intradermal injection may be administered to and/or around the vicinity of a lumbar nerve of the patient. The selected lumbar nerve comprises the l-1 nerve, l-2 nerve, l-3 nerve, l-4 nerve, l-5 nerve, or a combination thereof. The subcutaneous or intradermal injection may be administered to and/or around the vicinity of a sacral nerve of the patient. The selected sacral nerve comprises the s-1 nerve, s-2 nerve, s-3 nerve, s-4 nerve, s-5 nerve, or a combination thereof. In some embodiments, the subcutaneous or intradermal injection may be administered to and/or around the vicinity of a trigeminal nerve, a cervical nerve, a thoracic nerve, a lumbar nerve, a sacral nerve, or a combination thereof of the patient. Preferably, the administration for an adult who weighs about 150 lbs. comprises by subcutaneous or intradermal injection 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the l-1 to l-2, l-2 to l-3, and/or l-4 to l-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral). The dosage of botulinum toxin for an adult, a child or a toddler from about 1 to 5 years old is adjusted for age and weight. In some desired embodiments, the botulinum toxin comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. In further embodiments, a total dosage of the botulinum toxin for an adult who weighs about 150 lbs is between about 1 unit and about 150 units. A total dosage of the botulinum toxin for an adult, a child over about 5 years old, and a toddler from about 1 to 5 years old is adjusted for age, weight, or a combination thereof. In infants or toddlers—from about 1 to 5 years old, botulinum toxin is used to prevent or minimize damage to the developing brain; in older children and adult patients with dyslexia, botulinum toxin will be used to reduce or eliminate their symptoms.

DETAILED DESCRIPTION OF THE PREFERRED EMBODIMENTS

Further in relation to this, before explaining at least the preferred embodiments of the invention in greater detail, it is to be understood that the invention is not limited in its application to the details of construction and to the arrangements of the components set forth in the following description. It would be understood by those of ordinary skill in the art that embodiments beyond those described herein are contemplated, and the embodiments can be practiced and carried out in a plurality of ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, the term "about" means approximately or nearly and in the context of a numerical value or range set forth, herein means±10% of the numerical value or range recited or claimed.

The term "treating" includes delaying, alleviating, mitigating, or reducing the intensity, progression, or worsening of one or more attendant symptoms of a disorder or condition and/or alleviating, mitigating or impeding one or more causes of a disorder or condition. Treatment under the claimed invention may be a preventative treatment, prophylactic treatment, remission of treating or ameliorating treatment.

The term "therapeutically effective amount" or "therapeutically effective dose" refers to the amount of a composition, compound, therapy, or course of treatment that, when administered to an individual for treating a disorder or disease, is sufficient to effect such treatment for the disorder or disease. The "therapeutically effective amount" will vary depending on the composition, the compound, the therapy, the course of treatment, the disorder or disease, and its severity, and the age, weight, etc., of the individual to be treated.

The term "unit" refers to the amount of botulinum toxin needed to kill 50% of a group of 18-20 gm female swiss-webster mice given the injection intraperitoneally.

The term "vicinity of a nerve" refers to anywhere on the dermatome involved with the nerve.

In accordance with the principles of the present invention, use of botulinum toxin to treat dyslexia or reading developmental disorder (RDD) is provided.

Treatment of Dyslexia

Dyslexia or reading developmental disorder (RDD) is a brain-based difficulty in acquiring fluent reading skills and affects roughly 10-15% of the population. Dyslexia also affects reading accuracy, reading comprehension, spelling skills, and math skills. There are numerous definitions based on the number of symptoms from normal to severe or profound. Dyslexia is truly a spectrum of symptoms like autism. Treatments vary as much as the symptoms, but most include different types of reading instruction.

In general, dyslexia occurs when an individual has significant difficulty with speed and accuracy of word decoding. Comprehension of text and spelling are also affected. The diagnosis of dyslexia involves the use of reading tests, but the continuum of reading performance suggests that any cutoff point is arbitrary. The IQ score does not play a role in the diagnosis of dyslexia. The cognitive difficulties of dyslexics include problems with speech perception, basic sound recognition, and manipulation in a language, language memory, and learning the sounds of letters.

Dyslexia is a neurological condition with a genetic basis. There are abnormalities in the brains of dyslexic individuals. There are also differences in the electrophysiological and structural characteristics of the brains of dyslexics. Physicians play a particularly important role in recognizing children who are at risk for dyslexia and helping their parents obtain the proper assessment.

There are many complex issues to consider in developing an appropriate definition of dyslexia. One of the major problems is that there is no specific blood test or brain imaging result that can provide a diagnosis. A more fundamental issue is that reading ability is measured on a continuum and there is no cutoff score on a reading test that clearly divides individuals into dyslexic and non-dyslexic groups. Thus, the distinction between dyslexia and normal reading is arbitrary; where the cutoff point is drawn varies from study to study.

In discussing the arbitrary nature of dyslexia, Shaywitz et al noted: "[o]ur findings indicate that dyslexia is not an all-or-nothing phenomenon, but like hypertension and obesity, occurs in varying degrees of severity. Although limitations on resources may necessitate the imposition of cutoff points for the provision of services, physicians must recognize that such cutoffs may have no biological validity." Shaywitz S E, Escobar M D, Shaywitz B A, Fletcher J M, Makuch R. *Evidence that dyslexia may represent the lower tail of a normal distribution of reading ability*. N Engl J Med. 1992; 326:145-50.

The definition for dyslexia is as elusive as the problem. Like autism, dyslexia is truly a spectrum of symptoms that varies from what is genetically normal for an individual to severe or profound defects in information gathering by the senses and related defects in processing, storing, and using that information by the human brain. Dyslexia is not a vision problem because the blind who learn to read using braille can also be dyslexic. What is needed is a non-arbitrary method to test and treat the spectrum of symptoms that is dyslexia or reading developmental disorder (RDD): (i) a method to test for dyslexia in infants to 5.5 years old when the involved parts of the brain are developing, and a treatment to stop the damage to the involved parts of the child's brain, and (ii) a treatment for older children and adults that would help them reach the maximum potential of their abilities.

As previously mentioned, the exact cause of dyslexia is unknown but dyslexia seems to be associated with a combination of environmental and genetic factors. Environmental factors may include, but are not limited to, a neurodevelopment disorder that disrupts brain development. Clear cut cases may include, but are not limited to, Down's syndrome, Fragile X Syndrome, Tourette's, Fetal Alcohol Syndrome, Gene Deletion Syndrome, schizophrenia, autism, vision defects, measles, etc. Most cases of dyslexia, however, does not fall into the combination of environmental and genetic factors. The problems with reading accuracy, fluency, comprehension, spelling skills, and mathematics cannot be also fully accounted for by low IQ, visual acuity problems, neurological conditions, or limitations of educational opportunities.

One of the leading theories for the cause of dyslexia is that there are excess concentrations of the neuroexcitatory glutamate, Substance P, and CGRP in the developing brain and cerebrospinal fluid (CSF) of these afflicted children. Studies have shown elevated levels of the molecules in varying degrees in the brain, CSF, and blood of dyslexic children. This is believed to cause a condition called neuroexcitatory toxicity that can occur in children during a period of human development in which higher level brain structures are growing and interconnecting between birth and 5 years of age. The toxicity can damage the developing interconnecting neurons. Thus, the age of onset of the higher levels of glutamate, Substance P, and CGRP, the degree to which the levels are above normal, the genetic sensitivity to the higher levels, and the area of the brain affected could determine or account for the vast spectrum of symptoms that are present in dyslexia. Glutamate analogs that block glutamate receptors and stop excitatory effects have been tried and seemed to help dyslexic symptoms, but when used at higher concentrations, the analogs caused severe systemic effects because glutamate is one of the most common neurotransmitters in the body.

Another example of neuroexcitatory toxicity occurs when an embryo is exposed to neuroexcitatory chemicals such as methamphetamine, cocaine, and alcohol, which can cause damage to the embryo's developing brain. This can happen for example when a mother uses such drugs during pregnancy.

Substances that make nerves fire with less stimulation are called "excitatory." Substances that make nerves require more stimulation to fire are called "inhibitory." Examples of neuroexcitatory substances are nicotine, cocaine, methamphetamine, epinephrine, and glutamate. Examples of neuroinhibitory substances are serotonin, gamma-aminobutyric acid (GABA), narcotics, and other medications such as Lyrica (for nerve pain) and Valium (an anxiolytic/sedative). Too much inhibition of nerves can cause drowsiness and death. Too many excitatory compounds can cause nerves to fire too fast with the possibility of resulting pain, lack of sleep, light sensitivity, cell death, seizures, etc. (symptoms depend on the function of the specific nerves).

Blocking the production or disabling glutamate receptors has shown to cause severe side effects, which demands alternative methods to control the level of glutamate. The question is where does the excess glutamate come from? How do you get rid of excess glutamate without affecting normal glutamate levels inside neurons and its normal functions?

The excess glutamate in dyslexic children's blood, CSF, and brain is expected to be caused by a child being born with migraines, fibromyalgia, or related neuropathic conditions or developing these conditions between birth and 5 years of age, during which higher functioning structures of the brain are forming. In adults with migraines, fibromyalgia, and neuropathic conditions, the glutamate levels in the brain, blood, and CSF are elevated. Interestingly, physical symptoms that can be observed on a toddler, infant, or adult with dyslexia are the same as those of fibromyalgia, migraines, and neuropathic conditions—light sensitivity, dilated pupils, sensitivity to loud noises, sleep disturbances, hyperactivity, sensitivity to touch, depression, and anxiety.

In migraines and fibromyalgia, the source of the overproduction of glutamate is believed to be the neurostructural cells that surround the neurons. The neurostructural cells are the glial, satellite, and astrocyte cells. The mechanism is that Substance P, CGRP (calcitonin gene-related peptide), and glutamate are produced intracellularly by the ribosomes of these cells, packaged in vesicles, and transported to the cell membrane. Here, a specialized protein called SNAP25 and/or VAMP transports the Substance P, CGRP, and glutamate across the cell membrane and the molecules are released into the CSF. The Substance P, CGRP, and glutamate then act as ligands to the nerves and make the nerves fire with less stimulation (neuroexcitation). The only other place the SNAP25 and/or VAMP is known to be functional in the human body is at the neuromuscular junction in muscle cells where the junction releases vesicles with acetylcholine into the neuromuscular junction and causes muscles to contract. In normal glutamate, Substance P, and CGRP production in cells, glutamate, Substance P, and CGRP are used internally in the neurons and not released by the SNAP25 and/or VAMP into the CS spaces.

In particular, the excess glutamate, Substance P, and CGRP in the brain retards, damages, or causes malformation in the higher brain structures during development. After the upper levels of the human brain have finished forming, the damage to the brain forming from excessive levels of glutamate, Substance P, and CGRP cannot be repaired or changed. In addition, after the brain forms, the excess glutamate, Substance P, and CGRP can still cause problems. While the excess glutamate cannot cause further damage to the developed brain, the excess glutamate can still interfere with information gathering and processing by a condition called "neural noise" or "neural chatter." This is in keeping with the observation that elevated brain levels of glutamate lead to decreased reading ability.

Subcutaneous botulinum toxin injection or any other injection that allows the botulinum toxin to reach the unmyelinated sensory C fiber (e.g., intradermal injection, etc.) has been shown to lower the glutamate levels to normal in adult patients with migraines, fibromyalgia, and other neuropathic conditions.

Starting at birth, children can be tested for higher levels of Substance P, CGRP, and glutamate in the children's blood at routine checkups. If the level is higher than normal and the child shows the physical symptoms and is not meeting developmental milestones, the child can be treated subcutaneously or by any other injection that allows the botulinum toxin to reach the neurostructural cells in the dorsal root ganglia and trigeminal ganglia with botulinum toxin to reduce the excess glutamate and restore a normal developmental environment in the brain. The injected botulinum toxin will stop the overproduction of glutamate, Substance P, CGRP, and the neuroexcitatory effects the molecules produce in fibromyalgia, migraines, and other neuropathic conditions.

The methods according to embodiments of the present invention are novel and inventive as they allow for a minimal amount of botulinum toxin to be injected and still cover all dermatomes with no or minimal motor involvement. By using a subcutaneous or intradermal injection that reaches the unmyelinated C-fibers, it takes a lot less botulinum toxin to be absorbed into them as opposed to the myelinated nerves, and there are no motor nerves in the epithelium. Also, the injection at, for example, ½ to 1 inch from the patient's spine allows for a lower dose of botulinum toxin because there is a shorter distance to the dorsal root ganglia (approximately ¼ inch) for botulinum toxin to diffuse as compared to several feet if given in the arm or leg. The site is the only place in the body where the sensory and motor nerves are not in close proximity. This combination of low dose and separation of approximately 1 inch of bone and tissue between the motor and sensory nerves should minimize or eliminate any motor side effects. Furthermore, the methods according to embodiments of the present invention does not require vagus nerve injection. The only superficial exposure of the vagus nerve is Arnold's nerve, which is in the ear canal. It is a mixed motor and sensory nerve, and the motor component of it innervates the throat. If you inject botulinum toxin into or around the Arnold's nerve, you can generate speech and swallowing problems. The inventor(s) have found that there is enough anastomosis between the sensory cervical nerves, the trigeminal nerve, and the vagus nerve that botulinum toxin can reach the vagus ganglia and stop the overproduction of Substance P, glutamate, and CGRP.

To diagnose dyslexia, blood glutamate levels could be checked at regular doctor visits starting in infancy. Doctors should also make sure brain development milestones are being met. Physical symptoms are substantially the same in migraines, fibromyalgia, depression, dyslexia, ASD (autism), and other neuropathic disorders: a) light sensitivity (dilated pupils), b) sensitivity to loud noises, c) hyperactivity, d) sensitivity to touch (tight clothes, being held, etc.) and/or e) stomach issues such as unexplained IBS.

If a patient is diagnosed to experience dyslexia, he or she can be given botulinum toxin subcutaneously or by any other injection that allows the botulinum toxin to reach the dorsal root ganglia, trigeminal, and vagus nerves' mutual cells to prevent or alleviate related symptoms and/or blood tests to assess blood levels of Substance P, CGRP, and glutamate. Then periodically developmental milestones and neuropathic symptoms are monitored as well as glutamate levels. Monitoring glutamate levels is important particularly for infants because it would be difficult to evaluate the infants for developmental milestones and neuropathic symptoms because of their age. Thus, the method will allow doctors to know when the botulinum toxin needs to be re-administrated. The botulinum toxin injection can be given to and/or around the vicinity of a trigeminal nerve, a cervical nerve, a thoracic nerve, a lumbar nerve, and/or a sacral nerve of the patient. Preferably, it is not necessary to inject botulinum toxin to the cranial nerves because there is numerous anastomosis between the trigeminal nerves and the spinal nerves. The selected trigeminal nerve may include, but is not limited to, an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. In the facial dermatome, botulinum toxin is injected subcutaneously to the trigeminal nerve or around the vicinity of the trigeminal nerve because the trigeminal nerve is entirely sensory. In contrast, the facial nerve supplies motor innervations to the face and has no subcutaneous axons. Thus, injecting botulinum toxin to the trigeminal nerve minimizes muscular side effects. The selected cervical nerve may include, but is not limited to, the c-2 nerve, c-3 nerve, c-4 nerve, c-5 nerve, c-6 nerve, c-7 nerve, c-8 nerve, or a combination thereof. The selected thoracic nerve may include, but is not limited to, the t-2 to t-3 nerve, t-5 to t-6 nerve, t-7 to t-9 nerve, and/or t-10 to t-12 nerve, or a combination thereof. The selected lumbar nerve may include, but is not limited to, the l-1 to l-2 nerve, l-2 to l-3 nerve, and/or l-4 to l-5 nerve, or a combination thereof. The selected sacral nerve may include, but is not limited to, the s-1 to s-2, s-3 to s-4, and/or s-4 to s-5, or a combination thereof. For example, 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the l-1 to l-2, l-2 to l-3, and/or l-4 to l-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral) can be administered. While the administration site is about one-inch lateral to the patient's spine in the above embodiment, the distance can be more than 0 inches, about 0.1-3 inches, about 0.5-2.5 inches or about 1.0-2.0 inches. Alternatively, the distance can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 inches. The methods according to embodiments of the present invention are preferably applied to all or many of these locations. Depending on symptoms or conditions, the botulinum toxin used in embodiments of the present invention can be injected to a subset or subgroup of the locations described in embodiments of the present invention. In one embodiment, 3 injections of 2 units each distributed along each side of the neck in the cervical area on the trigeminal nerve, 1 injection of 2 units in the ophthalmic, maxillary, mandibular division subcutaneously and bilaterally. These dosages are for an adult who weighs about 150 lbs. The dosage for younger children with dyslexia would have to be adjusted for age and weight.

Botulinum toxin is given to lower the levels of Substance P, CGRP, and glutamate, and botulinum toxin normally begins to work after about three days, when injected about ½ to an inch from the spinal cord for all spinal injections. Many original studies described injections in the forearm or calf, which were found to take about 2 weeks to begin working. In contrast, when the injection is subcutaneously given near the dorsal root ganglion to reach unmyelinated C-fibers, the toxin only takes less than two weeks to reach the height of its effectiveness. This is because it is a shorter distance to diffuse into the unprotected axons to the cell body. It is important to inject botulinum toxin near the patient's spine because there is about one inch of tissue between the motor and sensory nerves there and no botulinum toxin reaches the motor nerves from the injection, which would cause motor side effects. In other words, the only place in the body where the motor and sensory nerves do not run in close proximity is where the nerves exit the patient's spine; sensory nerves exit the dorsal root and the motor nerves exit the ventral roots. Thus, injecting botulinum toxin near the patient's spine allows the use of botulinum toxin in all dermatomes without producing muscular side effects. For example, blood glutamate levels can be monitored to make sure that the levels have dropped to a normal level, and the dyslexic symptoms can be monitored to make sure the symptoms normalize as well. When the botulinum toxin wears off and blood tests show an increase in Substance P, glutamate, or CGRP and/or the symptoms begins to re-develop, more botulinum toxin can be given by injection to combat this effect. If levels/symptoms fail to normalize, then perhaps a small dose of one of the glutamate antagonists can be administered to help lower glutamate levels without producing or minimizing muscular side effects. For patients, as discussed, it is possible to use the claimed method to delay, alleviate, mitigate or reduce the intensity, progression, or worsening of one or more attendant symptoms of a disorder or condition, and/or the claimed method alleviates, mitigates or impedes one or more causes of a disorder or condition.

In general, the therapeutically effective dosage or amount can be, for example, about 1-150 units depending on the patient's body weight. The dosage for adults is, for example, about 1-150 units. For an adult, the dosage can be adjusted to the patient's body weight. For children over about 5 years old, which is generally after the age brain formation has ceased, the dosage can be adjusted to the patient's body weight and age. For toddlers (from about 1 to 5 years old), the dosage can be, for example, about 1-30 units and can be adjusted to the patient's body weight and age. This is an estimate, but 30 units is the maximum dosage that has been used safely since the 1990s in cerebral palsy infants and young children to control their severe muscle spasms.

If older children or adults are diagnosed to have dyslexia, the patients can be given botulinum toxin to reduce or eliminate symptoms of dyslexia and/or blood tests to assess blood levels of Substance P, CGRP, and glutamate. The botulinum toxin injection can be given to and/or around the vicinity of a trigeminal nerve, a cervical nerve, a thoracic nerve, a lumbar nerve, and/or a sacral nerve of the patient. The selected trigeminal nerve may include, but is not limited to, an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. The selected cervical nerve may include, but is not limited to, the c-2 nerve, c-3 nerve, c-4 nerve, c-5 nerve, c-6 nerve, c-7 nerve, c-8 nerve, or a combination thereof. The selected thoracic nerve may include, but is not limited to, the t-2 to t-3 nerve, t-5 to t-6 nerve, t-7 to t-9 nerve, and/or t-10 to t-12 nerve, or a combination thereof. The selected lumbar nerve may include, but is not limited to, the l-1 to l-2 nerve, l-2 to l-3 nerve, and/or l-4 to l-5 nerve, or a combination thereof. The selected sacral nerve may include, but is not limited to, the s-1 to s-2, s-3 to s-4, and/or s-4 to s-5, or a combination thereof. For example, 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the l-1 to l-2, l-2 to l-3, and/or l-4 to l-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral) can be administered. These dosages are for an adult who weighs about 150 lbs. The dosage for 0-5 years old would have to be adjusted for age and weight.

Botulinum toxin is given to lower the levels of Substance P, CGRP, and glutamate, and botulinum toxin normally begins to work after about three days. It normally takes the botulinum toxin about one to two weeks to reach the height of its effectiveness. For example, blood glutamate levels can be monitored to make sure that the levels drop to normal, and the patient's physical symptoms can be monitored to make sure the levels normalize as well. Normal blood glutamate levels are known to range from 40 to 60 uM. Alternatively, normal blood glutamate levels may be one a person skilled in the art would reasonably perceive. When the botulinum toxin wears off, blood tests show an increase in Substance P, glutamate, or CGRP, and/or the symptoms begins to redevelop, more botulinum toxin can be given to combat the symptoms of the condition. If levels/symptoms fail to normalize, then perhaps a small dose of one of the glutamate antagonists can be administered to help lower glutamate levels without producing side effects.

In general, the total dosage can be about 1-150 units depending on the patient's body weight. Preferably, the total dosage is about 20-150 units. Preferably, the total dosage for adults whose weight is 150 lbs is about 20-150 units. For children over about 5 years old, after which brain formation has generally ceased, the total dosage can be adjusted to the child's body weight.

In infants and toddlers from about birth to 5% years of age, lowering the level of neuroexcitatory peptides to normal levels should prevent or minimize damage to the developing areas of the brain involved in reading accuracy, reading comprehension, math skills, and spelling skills and help the skills reach their genetic potential. In older children and adults with dyslexic symptoms, lowering the level of brain glutamate, Substance P, and/or CGRP to normal levels will manage and control a condition called "neural chatter or neural noise". "Neural chatter" is caused by a varying level of sensitivity to reaching the firing threshold of nerves that are involved with the input of information into the brain, the processing of information in the brain, and the output of the information from the brain in the form of speech, writing, and mathematics. It is thought that varying levels of glutamate, Substance P, and/or CGRP above normal levels would cause the neural chatter. The resulting neural chatter would cause the brain to confuse or interrupt the input of information to the brain, the processing of information in the brain, and the export of information from the brain. An example of this would be the varying symptoms of migraines. The cause of migraines is also thought to be above normal levels of Substance P, glutamate, and CGRP in the upper and middle branches of the trigeminal nerve. Sometimes, such migraine patients have symptoms of severe headaches, light sensitivity, and painful headaches. Other times, they have moderate or no symptoms. It is believed that if the concentration of the neural excitatory peptides could be returned to a normal stable level, it should give dyslexic patients a better ability to input process and export information from the brain.

Botulinum toxins for use according to the present invention can be stored in lyophilized, vacuum dried form in containers under vacuum pressure or as stable liquids. Prior to lyophilization, the botulinum toxin can be combined with pharmaceutically acceptable excipients, stabilizers, and/or carriers, such as albumin. The lyophilized material can be reconstituted with saline or water to create a solution or composition containing the botulinum toxin to be administered to the patient.

Preferably, the botulinum neurotoxin is peripherally administered by administering it to or in the vicinity of the aforementioned nerve, or to the aforementioned nerve branch, or its ganglion nuclei. This method of administration permits the botulinum neurotoxin to be administered to and/or to affect select intracranial target tissues. Methods of administration include injection of a solution or composition containing the botulinum neurotoxin, as described above, and include implantation of a controlled release system that controllably releases the botulinum neurotoxin to the target trigeminal tissue. Such controlled release systems reduce the need for repeat injections. Diffusion of biological activity of botulinum toxin within a tissue appears to be a function of dose and can be graduated. Jankovic J., et al Therapy with Botulinum Toxin, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin primarily affects neural systems believed to be involved in a selected neuropsychiatric disorder and does not have negative adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor, and/or a translocation domain). By way of example, and not by way of limitation, a fragment of botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its effects within the cell. The pH of the target tissue is only temporarily lowered so that neuronal and/or glial injury is reduced.

The botulinum toxin used in the treatment in accordance with embodiments of the present invention comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. Because of different mechanisms and cleavage sites of botulinum toxins, the potency, dosage, or duration may vary depend on the type of botulinum toxins. The botulinum toxin can be used with other modulating drugs or chemicals. In further embodiments, the therapeutically effective amount of the botulinum toxin administered is between about 1 unit and about 150 units.

In some embodiments, a composition administered to a patient consists of botulinum toxin(s). Alternatively, a pharmaceutically active composition contained in a composition administered to a patient consists of botulinum toxin(s). The composition may additionally include, but not be limited to, a pharmaceutically inactive excipient, stabilizer and/or carrier. If lyophilized, the botulinum toxin may be reconstituted with saline or water to make a solution or composition to be administered to the patient. Alternatively, a composition administered to a patient comprises botulinum toxin(s) and other pharmaceutically active ingredients.

Illustrative embodiments are explained in the following example of a case study conducted in a patient with dyslexia.

Example 1

Patient is a 49-year-old male. The patient weighs about 210 lbs. He has suffered from dyslexia all his life. He was administered botulinum toxin A in the area of trigeminal nerve and cervical nerve (2 units in ophthalmic, 2 units in maxillary, 2 units in mandibular of trigeminal nerve bilaterally; 2 units in the c-2-c-3, 2 units in the c-5-c-6, 2 units in the c-7-c-8 of cervical nerve bilateral for a total of 24 units). After one week from the administration, he reported noticing slight changes. After 2 weeks, he reported the following changes: i) easier to concentrate and focus; ii) able to stay on task 3 times longer than before; iii) much easier and clearer reading without as much mental strain; iv) better comprehension and retention of what he reads; and v) able to read at least twice as much as before without mental tiredness.

Example 2

Patient is a 25-year-old male. The patient weighs about 250 lbs. He was diagnosed with dyslexia, high functioning autism, and migraines. He was administered botulinum toxin A in the area of trigeminal nerve and cervical nerve (2 units in ophthalmic, 2 units in maxillary, 2 units in mandibular of trigeminal nerve bilaterally; 2 units in the c-2-c3, 2 units in the c-5-c-6, 2 units in the c-7-c-8 of cervical nerve bilateral for a total of 24 units). Since first week after the injection, he reported the following changes: i) no migraine has been reported; ii) able to read more and faster with better retention; and iii) better focusing on what he is doing (e.g., taking driving lessons). He also reported that he can now solve simple math problems in his head such as 2×15=30 which he could not do before.

Unless defined otherwise, all technical and scientific terms used herein have same meaning as commonly understood by the person of ordinary skill in the art to which this invention belongs.

It is understood that the above description of the invention and specific examples, while indicating preferred embodiments of the present invention, are given by way of illustration and not limitation. Many changes and modifications within the scope of the present invention may be made without departing from the spirit thereof, and the present invention includes all such changes and modifications.

What is claimed is:

1. A method for treating dyslexia or reading developmental disorder (RDD) in a patient in need thereof, comprising administering botulinum toxin to the patient, thereby treating dyslexia or reading developmental disorder (RDD),
    wherein administering for an adult comprises, by subcutaneous or intradermal injection, 2-4 units to and/or around the vicinity of a trigeminal nerve, 2-4 units to and/or around the vicinity of a cervical nerve, lateral to the patient's spine, 2-4 units to and/or around the vicinity of a thoracic nerve, lateral to the patient's spine, 2-4 units to and/or around the vicinity of a lumbar nerve, lateral to the patient's spine, and/or 2-4 units to and/or around the vicinity of a sacral nerve, lateral to the patient's spine.

2. The method of claim 1, wherein the trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof.

3. The method of claim 1, wherein the cervical nerve comprises a c-2 nerve, c-3 nerve, c-4 nerve, c-5 nerve, c-6 nerve, c-7 nerve, c-8 nerve, or a combination thereof.

4. The method of claim 1, wherein the thoracic nerve comprises a t-2 nerve, t-3 nerve, t-5 nerve, t-6 nerve, t-7 nerve, t-8 nerve, t-9 nerve, t-10 nerve, t-11 nerve, t-12 nerve, or a combination thereof.

5. The method of claim 1, wherein the lumbar nerve comprises an l-1 nerve, l-2 nerve, l-3 nerve, l-4 nerve, l-5 nerve, or a combination thereof.

6. The method of claim 1, wherein the sacral nerve comprises an s-1 nerve, s-2 nerve, s-3 nerve, s-4 nerve, s-5 nerve, or a combination thereof.

7. The method of claim 1, wherein the botulinum toxin comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof.

8. The method of claim 1, wherein each of the subcutaneous or intradermal injection is bilateral.

9. The method of claim 1, wherein a total dosage of the botulinum toxin for an adult who weighs about 150 lbs is between about 2 units and about 150 units.

10. The method of claim 1, wherein a total dosage of the botulinum toxin for an adult, a child over about 5 years old, and a toddler from about 1 to 5 years old is adjusted for age, weight, or a combination thereof.

11. The method of claim 1 wherein the patient is a toddler from about birth to 5 years old.

12. The method of claim 1 reduces or eliminates a symptom of dyslexia or reading developmental disorder (RDD) in a child over about 5 years old and an adult.

13. A method for treating dyslexia or reading developmental disorder (RDD) in a patient in need thereof, comprising administering botulinum toxin to the patient, thereby treating dyslexia or reading developmental disorder (RDD),
    wherein administering for an adult comprises, by subcutaneous or intradermal injection, 2-4 units to and/or around the vicinity of a trigeminal nerve, 2-4 units to and/or around the vicinity of a cervical nerve, lateral to the patient's spine, 2-4 units to and/or around the vicinity of a thoracic nerve, lateral to the patient's spine, 2-4 units to and/or around the vicinity of a lumbar nerve, lateral to the patient's spine, and/or 2-4 units to and/or around the vicinity of a sacral nerve, lateral to the patient's spine,
    wherein a maximum total dosage of the botulinum toxin is 150 units.

14. The method of claim 13, wherein the trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof.

15. The method of claim 13, wherein the cervical nerve comprises a c-2 nerve, c-3 nerve, c-4 nerve, c-5 nerve, c-6 nerve, c-7 nerve, c-8 nerve, or a combination thereof.

16. The method of claim 13, wherein the thoracic nerve comprises a t-2 nerve, t-3 nerve, t-5 nerve, t-6 nerve, t-7 nerve, t-8 nerve, t-9 nerve, t-10 nerve, t-11 nerve, t-12 nerve, or a combination thereof.

17. The method of claim 13, wherein the lumbar nerve comprises an l-1 nerve, l-2 nerve, l-3 nerve, l-4 nerve, l-5 nerve, or a combination thereof.

18. The method of claim 13, wherein the sacral nerve comprises an s-1 nerve, s-2 nerve, s-3 nerve, s-4 nerve, s-5 nerve, or a combination thereof.

19. The method of claim 13, wherein the botulinum toxin comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof.

20. The method of claim 13, wherein each of the subcutaneous or intradermal injection is bilateral.

* * * * *